(12) United States Patent
Macklin et al.

(10) Patent No.: US 8,559,669 B2
(45) Date of Patent: Oct. 15, 2013

(54) SECURITY POLYMER THREAT DETECTION DISTRIBUTION SYSTEM

(75) Inventors: Jon D. Macklin, El Cajon, CA (US); Walter C. Bonneau, Jr., Escondido, CA (US); Jonathan P. Gluckman, Columbia, MD (US); Igor Dorovskoy, Columbia, MD (US)

(73) Assignee: Cubic Corporation, San Diego, CA (US)

( * ) Notice: Subject to any disclaimer, the term of this patent is extended or adjusted under 35 U.S.C. 154(b) by 178 days.

(21) Appl. No.: 13/037,997

(22) Filed: Mar. 1, 2011

(65) Prior Publication Data

US 2012/0057741 A1 Mar. 8, 2012

Related U.S. Application Data

(60) Provisional application No. 61/309,404, filed on Mar. 1, 2010.

(51) Int. Cl.
*G06K 9/00* (2006.01)

(52) U.S. Cl.
USPC .......................................................... 382/100

(58) Field of Classification Search
USPC .......................................................... 382/100
See application file for complete search history.

(56) References Cited

U.S. PATENT DOCUMENTS

| | | | |
|---|---|---|---|
| 4,821,118 A | 4/1989 | Lafreniere et al. | |
| 4,975,222 A | 12/1990 | Yoshino et al. | |
| 5,200,614 A | 4/1993 | Jenkins | |
| 5,491,326 A | 2/1996 | Marceau et al. | |
| 5,491,337 A | 2/1996 | Jenkins et al. | |
| 5,722,835 A | 3/1998 | Pike | |
| 5,741,984 A | 4/1998 | Danylewych-May et al. | |
| 5,818,047 A | 10/1998 | Chaney et al. | |
| 6,073,499 A | 6/2000 | Settles | |
| 6,765,198 B2 | 7/2004 | Jenkins et al. | |

(Continued)

FOREIGN PATENT DOCUMENTS

| | | |
|---|---|---|
| DE | 4322274 A1 | 12/1995 |
| EP | 0599291 | 6/1994 |

(Continued)

OTHER PUBLICATIONS

"Explosives and Narcotics Detection—EntryScan3" retrieved off internet http://www.geindustrial.com/ge-interlogix/iontrack/prod_entryscan.html on Dec. 2, 2005, 1 page.

(Continued)

*Primary Examiner* — Tom Y Lu
(74) *Attorney, Agent, or Firm* — Kilpatrick Townsend & Stockton LLP

(57) ABSTRACT

Embodiments disclosed enable the detection of the presence of chemical, biological, and/or explosive (CBE) substance or other items of interest on individuals handling tickets, fobs, passes, smartcards, or other media. Embodiments generally contemplate issuing media at a first location and analyzing the media at a second location. Material sensitive to CBE substance can be applied to the media at the first and/or second location. An adhesive also may be used to attract and/or retain particles to the media for analysis and/or adhere the detection material to the media. Such embodiments can be utilized in airports, transit stations, and other applications where security against threats posed by CBE substance may be a concern.

33 Claims, 13 Drawing Sheets

(56) References Cited

U.S. PATENT DOCUMENTS

| | | | |
|---|---|---|---|
| 6,855,473 B2* | 2/2005 | Odamura et al. | 430/200 |
| 6,914,668 B2 | 7/2005 | Brestel et al. | |
| 6,952,163 B2 | 10/2005 | Huey et al. | |
| 6,975,227 B1 | 12/2005 | Nishikawa et al. | |
| 6,995,839 B1 | 2/2006 | Shapiro | |
| 7,047,829 B2 | 5/2006 | Napoli | |
| 7,063,924 B2* | 6/2006 | Kaminsky et al. | 430/10 |
| 7,109,859 B2 | 9/2006 | Peeters | |
| 7,116,798 B1 | 10/2006 | Chawla | |
| 7,139,406 B2 | 11/2006 | McClelland et al. | |
| 7,212,113 B2 | 5/2007 | Zanovitch | |
| 7,271,720 B2 | 9/2007 | Tabe | |
| 7,367,494 B2 | 5/2008 | Macklin et al. | |
| 7,491,948 B2 | 2/2009 | Gordon et al. | |
| 7,522,040 B2 | 4/2009 | Passmore et al. | |
| 7,677,449 B2 | 3/2010 | Macklin et al. | |
| 7,801,833 B2 | 9/2010 | Bhatt et al. | |
| 7,934,645 B2 | 5/2011 | Macklin et al. | |
| 7,936,265 B2 | 5/2011 | Macklin et al. | |
| 8,205,796 B2 | 6/2012 | Macklin et al. | |
| 2002/0024450 A1 | 2/2002 | Townsend et al. | |
| 2002/0084900 A1 | 7/2002 | Peterson et al. | |
| 2003/0028814 A1 | 2/2003 | Carta et al. | |
| 2003/0128099 A1 | 7/2003 | Cockerham | |
| 2003/0143119 A1 | 7/2003 | Schwartz et al. | |
| 2004/0073439 A1 | 4/2004 | Shuster | |
| 2004/0117638 A1 | 6/2004 | Monroe | |
| 2004/0165750 A1 | 8/2004 | Chew | |
| 2004/0169076 A1 | 9/2004 | Beale et al. | |
| 2004/0190757 A1 | 9/2004 | Murphy et al. | |
| 2004/0204915 A1 | 10/2004 | Steinthal et al. | |
| 2004/0227929 A1 | 11/2004 | Brestel et al. | |
| 2005/0019220 A1 | 1/2005 | Napoli | |
| 2005/0022581 A1 | 2/2005 | Sunshine | |
| 2005/0088299 A1 | 4/2005 | Bandy et al. | |
| 2005/0137890 A1 | 6/2005 | Bhatt et al. | |
| 2005/0288937 A1 | 12/2005 | Verdiramo | |
| 2006/0073312 A1* | 4/2006 | Hattori | 428/195.1 |
| 2006/0180647 A1 | 8/2006 | Hansen | |
| 2006/0243796 A1 | 11/2006 | Macklin et al. | |
| 2006/0290496 A1 | 12/2006 | Peeters | |
| 2007/0102294 A1 | 5/2007 | Dorisio et al. | |
| 2008/0286802 A1 | 11/2008 | Terry et al. | |
| 2009/0072024 A1 | 3/2009 | Bonneau, Jr. et al. | |
| 2009/0115605 A1 | 5/2009 | Ravenis, II et al. | |
| 2009/0219390 A1 | 9/2009 | Dugan et al. | |
| 2010/0219932 A1 | 9/2010 | Macklin et al. | |
| 2011/0115464 A1 | 5/2011 | Bonneau, Jr. et al. | |
| 2012/0112878 A1 | 5/2012 | Macklin et al. | |

FOREIGN PATENT DOCUMENTS

| | | |
|---|---|---|
| EP | 1182622 A1 | 2/2002 |
| WO | 03/075119 A2 | 9/2003 |
| WO | 03/091945 A | 11/2003 |
| WO | WO 2004/114242 A1 | 12/2004 |
| WO | WO 2006/035392 A1 | 4/2006 |
| WO | WO 2006/096246 A1 | 9/2006 |
| WO | WO 2006/130528 A1 | 12/2006 |
| WO | WO 2007/081922 A2 | 7/2007 |
| WO | 2009/021236 A1 | 2/2009 |
| WO | 2009/025894 A1 | 2/2009 |

OTHER PUBLICATIONS

"Explosives and Narcotics Detection—Itemiser3" retrieved off internet http://www.geindustrial.com/ge-interlogix/iontrack/prod_itemiser.html on Dec. 2, 2005, 1 page.

"Explosives and Narcotics Detection—StreetLab," retrieved off internet http://www.geindustrial.com/ge-interlogix/iontrack/prod_streetlab.html on Dec. 2, 2005, 1 page.

"Explosives and Narcotics Detection—VaporTracer2" retrieved off internet http://www.geindustrial.com/ge-interlogix/iontrack/prod_vaportracer.html on Dec. 2, 2005, 1 page.

"Explosives and Narcotics Detection," retrieved off internet http://www.geindustrial.com/ge-interlogix/iontrack/prod_tech_overview.html on Dec. 2, 2005, 1 page.

International Search Report and Written Opinion dated Apr. 11, 2011 for International Application No. PCT/US2011/26728, 7 pages.

* cited by examiner

External Layer(s) (Front/Back)

Inlay Core

Non-Wireless

SECURITY POLYMER THREAT DETECTION DISTRIBUTION SYSTEM

The present application claims benefit under 35 USC 119 (e) of U.S. Provisional Patent Application No. 61/309,404, filed Mar. 1, 2010 for "SECURITY POLYMER THREAT DETECTION DISTRIBUTION SYSTEM" which is incorporated by reference in its entirety for all purposes.

BACKGROUND OF THE INVENTION

This disclosure relates in general to chemical, biological, and explosive detection and, but not by way of limitation, to detection by determining exposure of a media.

Analysis in most current detection systems employs ion mobility spectroscopy as the mechanism for detecting items of interest. The detection capture and analysis devices may be installed in the infrastructure being protected such as at the portals for entry or exit, positioned to capture from the persons involved through contact (e.g., touch or swipe) or may be handheld and employed by those protecting the infrastructure. Such devices are common in airports today. The devices typically are slow in the capture and analysis process, frequently require operator participation and require regular cleaning, potentially after each use. In addition, the analysis results are frequently ambiguous, resulting in high false alarm rates. Rates of false alarms for ion mobility spectrometry is approximately 2%.

Detection of trace particles or emanations from compounds which may represent a threat to the public is based on the capture and analysis of the material. Capture may be accomplished through contact (e.g., wipe a surface or contact with a capture surface) or through capture from the atmosphere (e.g., forced air flow such as a "puffer" to dislodge particles from surfaces or through vapor sampling from the atmosphere).

An emerging class of detection devices relies on the capture of the threat indicating material causing a change in the composition of the material of the device which captures it. The change is then observable or causes a detectable change in the reflective photo luminescence. Optical scanners may be employed to detect the change in luminescence when the capture material is presented. In cases where the change in the capture material is visible, the holder may dispose of the device before the capture event is recorded or associated with the person.

BRIEF SUMMARY OF THE INVENTION

Embodiments described herein enable the detection of the presence of chemical, biological, and/or explosive (CBE) substance or other items of interest on individuals handling tickets, fobs, passes, smartcards, mobile devices, or other media. Embodiments generally contemplate issuing and processing media at a first location and analyzing the media at a second location. Material sensitive to CBE substance can be applied to the media at the first and/or second location. An adhesive may also be used in conjunction with the detection material to bond a detection material carrier to the media for analysis. Such embodiments can be utilized in airports, transit stations, and other applications where security against threats posed by CBE substance may be a concern.

One embodiment provides for a method of determining exposure of a media to an item of interest. The method includes providing the media at a first location, where the media has a unique identifier, and determining the unique identifier of the media at a second location. The method further includes creating a first image of the media, and applying, to the media, detection material sensitive to the item of interest. The item of interest can be one of a chemical, a biologic compound, or an explosive, and the applying can occur at the second location. The method also includes creating, at the second location, a second image of the media, and analyzing the first image and the second image to determine if the detection material has sensed the item of interest. The analyzing can include determining an optical change between the first image and the second image. Finally, the method includes indicating a result based, at least in part, on the analyzing.

The method of determining exposure of a media can include one or more of the following features. The first image of the media, the second image of the media, or both, can utilize at least one optical technology from the group consisting of a charge coupled device (CCD), a digital light processor (DLP), and an infrared (IR) sensor. Creating the first image of the media can occur at the second location. Determining an identity of a user. Associating the identity of the user with the unique identifier of the media. Verifying, at the second location, the identity of the user. The determining the identity of the user can include capturing a picture of the user. Determining the unique identifier of the media at the second location can include using at least one technology from the group consisting of radio frequency identification (RFID), bar code scanning, optical imaging, and magnetic stripe reading.

The for a method of determining exposure of a media further contemplates including one or more of the following features. Applying detection material to the media includes using an adhesive frame, sticker, magazine, or roll feed. Creating, at the second location, an adhesive area on the media. Creating the adhesive area on the media including at least one of applying an adhesive material to the media, or exposing an adhesive material of the media. The adhesive area can cause adhesion of particles using at least one of chemical adhesion, or electrical charge.

Another embodiment provides for a device for determining exposure of a media to an item of interest, the device comprising a media imager configured to create at least one image of the media and a detection material applicator configured to apply, to the media, detection material sensitive to the item of interest. The item of interest can be one of a chemical, a biologic compound, or an explosive. The device further comprises a processing unit configured to analyze the at least one image of the media to determine if the detection material has sensed the item of interest based, at least in part, on an optical characteristic of the detection material in the at least one image. Finally, the device comprises, an analysis indicator configured to indicate a result based, at least in part, on an analysis of the at least one image of the media.

The device for determining exposure of the media to the item of interest can include one or more of the following features. The media imager can be configured to create a first image and a second image, the first image being created before the detection material is applied to the media, and the second image being created after the detection material is applied to the media. The processing unit can be configured to determine if the detection material has sensed the item of interest based, at least in part, on an optical change of the detection material between the first image and the second image. A camera can be configured to capture a picture of a user of the media. A media reader can be configured to determine a unique identifier of the media. An identification verifier can be configured to verify an identity of a user of the media. The processing unit can be further configured to verify the identity of the user of the media based, at least in part, on a picture of the user and the unique identifier of the media.

The device for determining exposure of the media to the item of interest further can include one or more of the following features. The media reader can include at least one device from the group consisting of a radio frequency identification (RFID) reader, a bar code scanner, an optical imager, and a magnetic stripe reader. The detection material applicator can be configured to use an adhesive frame, sticker, magazine, or roll feed application. The analysis indicator can include at least one item from the group consisting of a display, a light-emitting diode (LED), a speaker, and a network interface.

Another embodiment provides for a non-transitory machine-readable storage medium comprising instructions embodied thereon that, when executed by at least one machine, cause the at least one machine to determine a unique identifier of the media and create a first image of the media. The instructions also cause the at least one machine to apply, to the media, detection material sensitive to the item of interest. The item of interest can be one of a chemical, a biologic compound, or an explosive. The instructions further cause the at least one machine to create a second image of the media and analyze the first image and the second image to determine if the detection material has sensed the item of interest. The analyzing can include determining an optical change between the first image and the second image. Finally, the instructions also cause the at least one machine to indicate a result based, at least in part, on the analyzing.

The non-transitory machine-readable storage medium can further cause the at least one machine to perform one or more of the following functions. Provide the media at a first location; and create the first image of the media at a second location. Determine an identity of a user. Associate the identity of the user with the unique identifier of the media. Associating the identity of the user with the unique identifier of the media can be configured to occur at a first location; and the instructions, when executed by at least one machine, further can cause the at least one machine to verify, at a second location, the identity of the user. Determining the identity of the user can include capturing a picture of the user. Determining the unique identifier of the media includes using at least one technology from the group consisting of radio frequency identification (RFID), bar code scanning, optical imaging, and magnetic stripe reading. Apply the detection material to the media includes using an adhesive frame, sticker, magazine, or roll feed application. Create an adhesive area on the media. Creating the adhesive area on the media can include at least one of applying an adhesive material to the media, or exposing an adhesive material of the media. The adhesive area can be created to adhere particles using at least one of chemical adhesion, or electrical charge.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures.

Figure 1A:
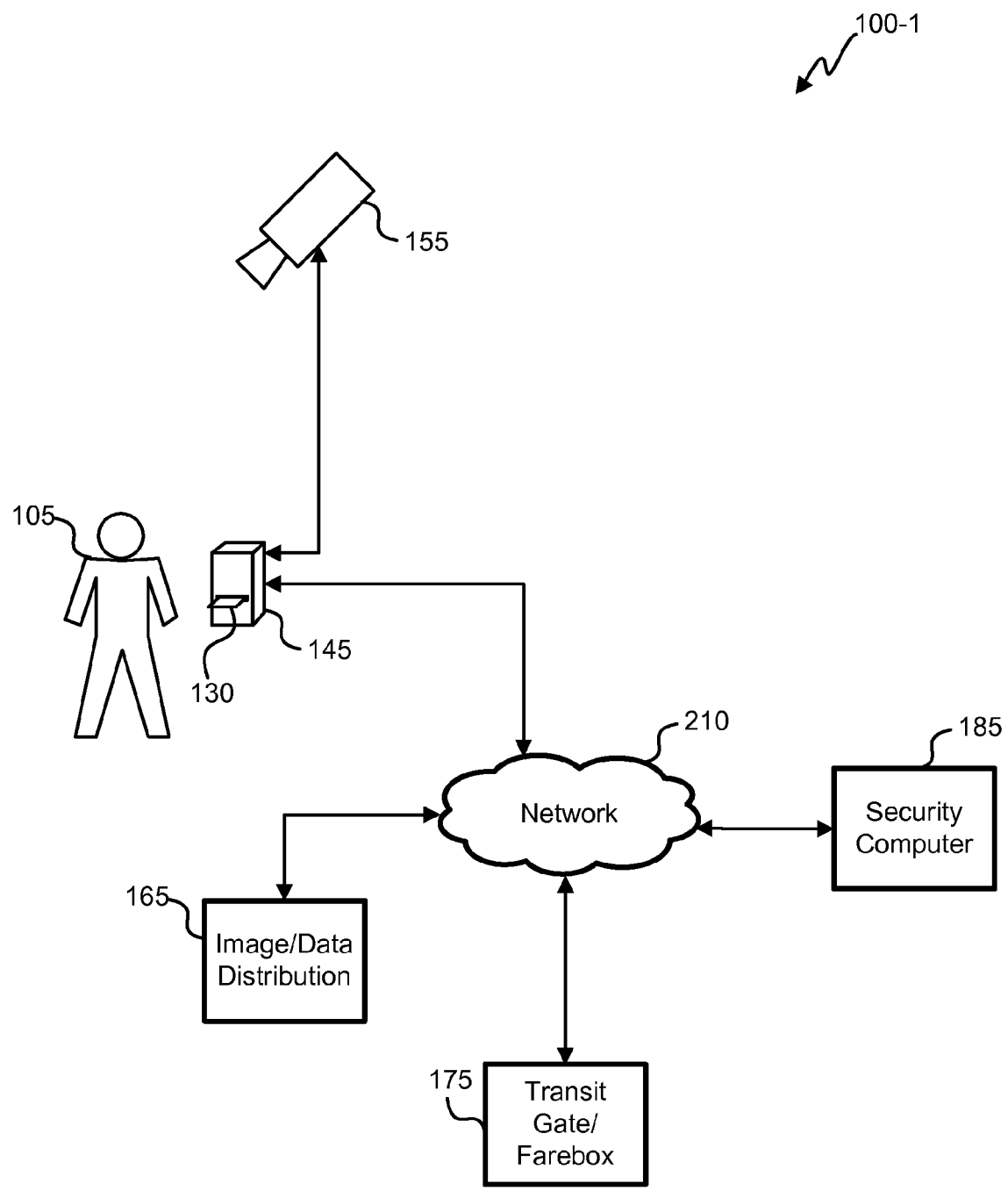
FIG. 1A is a simplified illustration diagram of an embodiment of a detection system in public transit system.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It being understood that various changes may be made in the function and arrangement of elements without departing from the spirit and scope as set forth in the appended claims.

A detection material using a polymer sensor technology provides detection of a chemical, biological and/or explosive (CBE) substance, also referred to hereinafter as an "item of interest." This detection material can include different technologies, such as but not limited to, molecularly imprinted polymer (MIP) technology that can register detection of an item of interest that has come in contact with the media using organic and/or inorganic polymers created to detect certain molecules and/or molecule groups. Upon detection, the physical characteristics of the detection material, such as color (including non-visible spectra, such as infrared), transparency, magnetic and/or electrical conductivity, can change. Thus, one or more images and/or electrical readings of the material can be taken and used to determine a change in a physical characteristic of the detection material, thereby indicating detection of an item of interest. Because detection material can be configured to detect a specific item of interest substance, multiple detection materials can be applied to the media to detect multiple items of interest. In addition to being able to detect the item(s) of interest, some embodiments also provide an indication of the volume or strength of trace materials detected.

Detection materials include polymers that are currently available to detect a particular item of interest. They could include vapor or particulate sensing polymers, florescent quenching polymers, and/or Molecularly Imprinted Polymers (MIP). Current classifications of sensing would include CBE substances. The molecular formula and the electrical properties for each classification of substances vary, as well as the formulations for each subclass. For example, the molecular formula for a MIP polymer that detects TNT will vary from the molecular formula for the MIP polymer that detects RDX. These differing formulas cause physical properties of a MIP polymer to react differently upon exposure. The value of the exposure information can be a value indicative of the amount of exposure experienced. The characteristics of the MIP can be such that a physical characteristic or electrical characteristic changes as a function of exposure.

The use of detection materials, applied to and/or embedded in a media as described herein, can be utilized in any of a variety of security applications. For example, and not by way of limitation, FIG. 1A is a simplified block diagram of a detection system 100-1 that can be used in a public transit system. In this embodiment, a transit passenger 105 who has been issued a ticket/media 130 can insert the ticket/media 130 into the validator unit 145. Along with validating the ticket/media 130, the validator unit 145 can utilize techniques described herein to apply a detection material to the ticket/media 130 and determine whether the ticket/media 130 has been exposed to any items of interest while in the custody of the transit passenger 145.

The validator unit 145 can then reissue the ticket/media 130 to the transit passenger 105, or capture the media. The determination of whether to reissue or capture the ticket/media 130 can be based on whether the ticket/media 130 was exposed to an item of interest, a level of exposure, a type of exposure, which may be considered with additional information (e.g., a current security threat level, information regarding the transit passenger 145, a time of day, a condition of the media (e.g., if damaged or purposefully altered to reduce readability), etc.). Furthermore, information may be written to the media/ticket 130 before reissuance or capture, which can include a flag or other information regarding detection/non-detection of an item of interest along with other information (e.g., validation information) that can provide additional functionality in the transit system.

In this embodiment, the validator unit 145 can be connected with various other components of the detection system 100-1 either directly or via a network 210. For example, the validator unit 145 can communicate with a camera 155 to capture a picture and/or video of the transit passenger 105. The captured picture and/or video can be associated with the ticket/media 130 provided by the transit passenger 105 to allow the detection system 100-1 to have a form of passenger identification associated with the picture and/or video.

Other components of the detection system 100-1 can provide added functionality in a transit system context. For example, information regarding detection/non-detection of an item of interest, along with images from the camera 155 and other information associated with the media/ticket 130, may be sent to a security computer 185 for further analysis, processing, security measures, and/or archival. The validator unit 145 and/or security computer 185 can further communicate information to one or more transit gate/fareboxes 175. This can, for example, enable the transit gate/fareboxes 175 to deny access to a media/ticket 130 that has been flagged by the detection system 100-1. Additionally or alternatively, a transit gate/farebox 175 can deny access if the transit gate/farebox 175 reads information from the ticket/media 130 that the ticket/media 130 has been flagged.

The detection system 100-1 can also include an image/data distribution system 165. The image/data distribution system 165 can be used to distribute information to help ensure the security of the transit system. For example, if a media/ticket 130 is flagged, the image/data distribution system 165 can send captured images or video of the transit passenger 105, and/or other data associated with the flagged ticket/media 130, to police, security, transit personnel, etc. Such alerts can be sent from a computer or other processing device using short message service (SMS), email, telephone, or the Internet to computers, terminals, cellphones, mobile devices, etc.

Figure 1B:
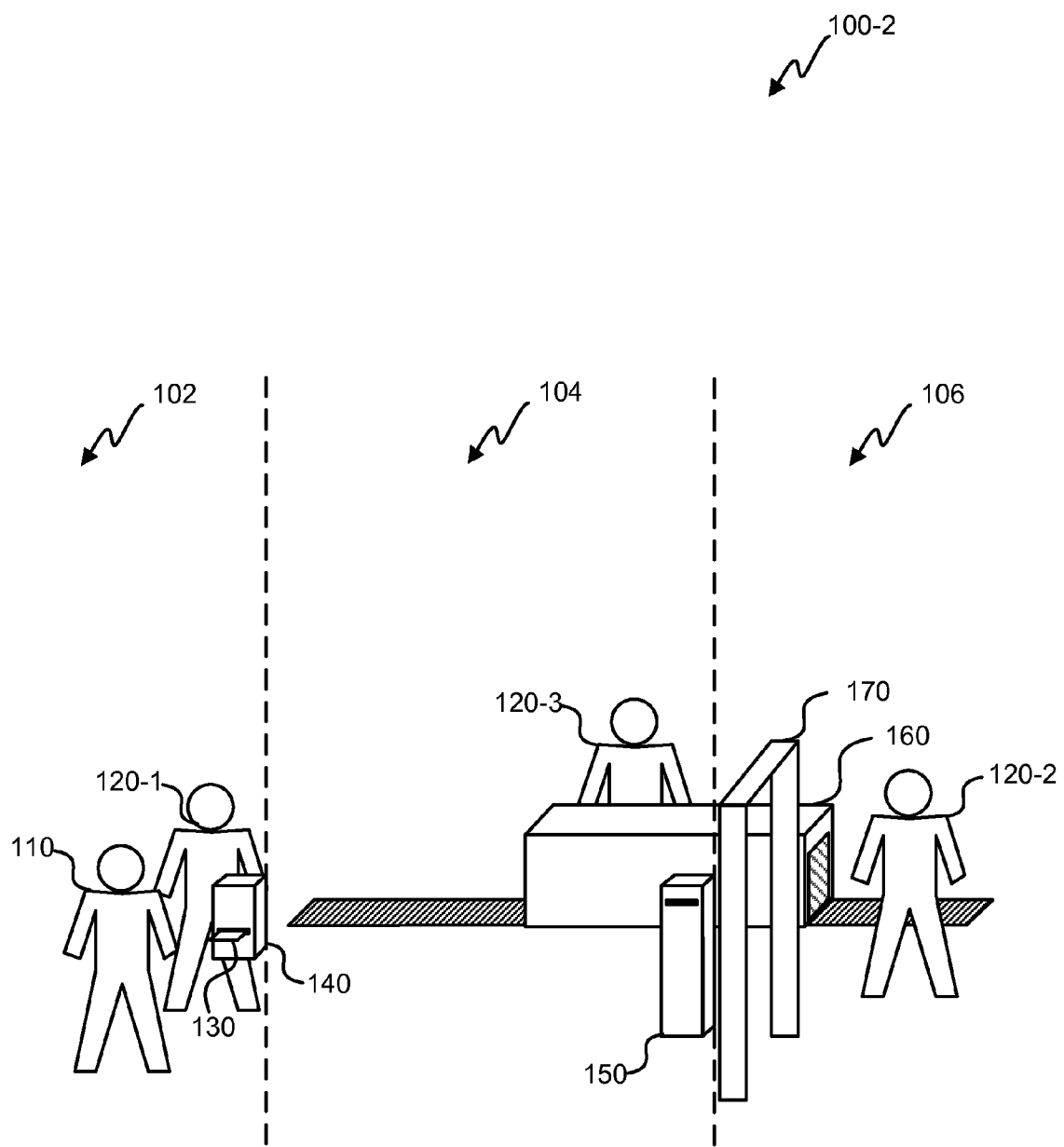
FIG. 1B is a simplified illustration diagram of an embodiment of a detection system in an airport security line.

FIG. 1B is a simplified illustration of another embodiment of a detection system 100-2. In particular, but not by way of limitation, FIG. 1B provides an overview of how detection materials can be used to help enhance security in an airport security line. In this embodiment, a passenger 110 is issued a ticket/media 130 by a ticket/media dispenser 140 when moving from an unsecured area 102 to a semi-secure area 104. The ticket/media dispensing can be overseen and/or operated by a first security worker 120-1. The ticket/media dispenser 140 can be, for example, integrated into a first security checkpoint, in which the first security worker 120-1 checks identification of the passenger 110. The identification of the passenger 110 can be automatically or manually associated with the ticket/media 130 issued to the passenger 110, and the ticket/media 130 can include a unique identifier for later identification of the ticket/media 130. Moreover, the ticket/media 130 can include a detection material to detect exposure to an item of interest.

The passenger 110 then moves though the semi-secure area 104, exposing the ticket/media 130 to trace amounts of substances (in a process called "sample harvesting") on the passenger's hands, clothes, luggage, etc. When attempting to enter a secure area 106 from the semi-secure area 104, the passenger 110 can enter the ticket/media 130 into a ticket/media analyzer 150 and optionally pass through other security measures, such as a metal detector 170 or similar device. The media/ticket analyzer 150 can analyze the detection material of the ticket/media 130 to determine whether the ticket/media 130 was exposed to any items of interest. The ticket analyzer 150 can also validate and/or mutually authenticate the ticket/media 130 and compare to the initial issuance record of the ticket/media dispenser 140. The ticket/media 130 analyzer 150 can then indicate to a second security worker 120-2 a result of the analysis (e.g., whether an item of interest was detected, a level of exposure of the ticket/media 130 to an item of interest, etc.).

Additionally or alternatively embodiments can integrate CBE detection with a luggage screener 160 to determine whether luggage, trays, or other items travelling through the luggage screener 160 have been exposed to an item of interest. Depending on the type of detection material used, such analysis may have to occur before the ticket/media 130 is exposed to x-rays or other security measures that could alter the detection material, thereby adversely impacting the accuracy of the analysis. The result of the analysis could be provided to a security worker 120-3 operating the luggage screener 160.

Figure 2A:
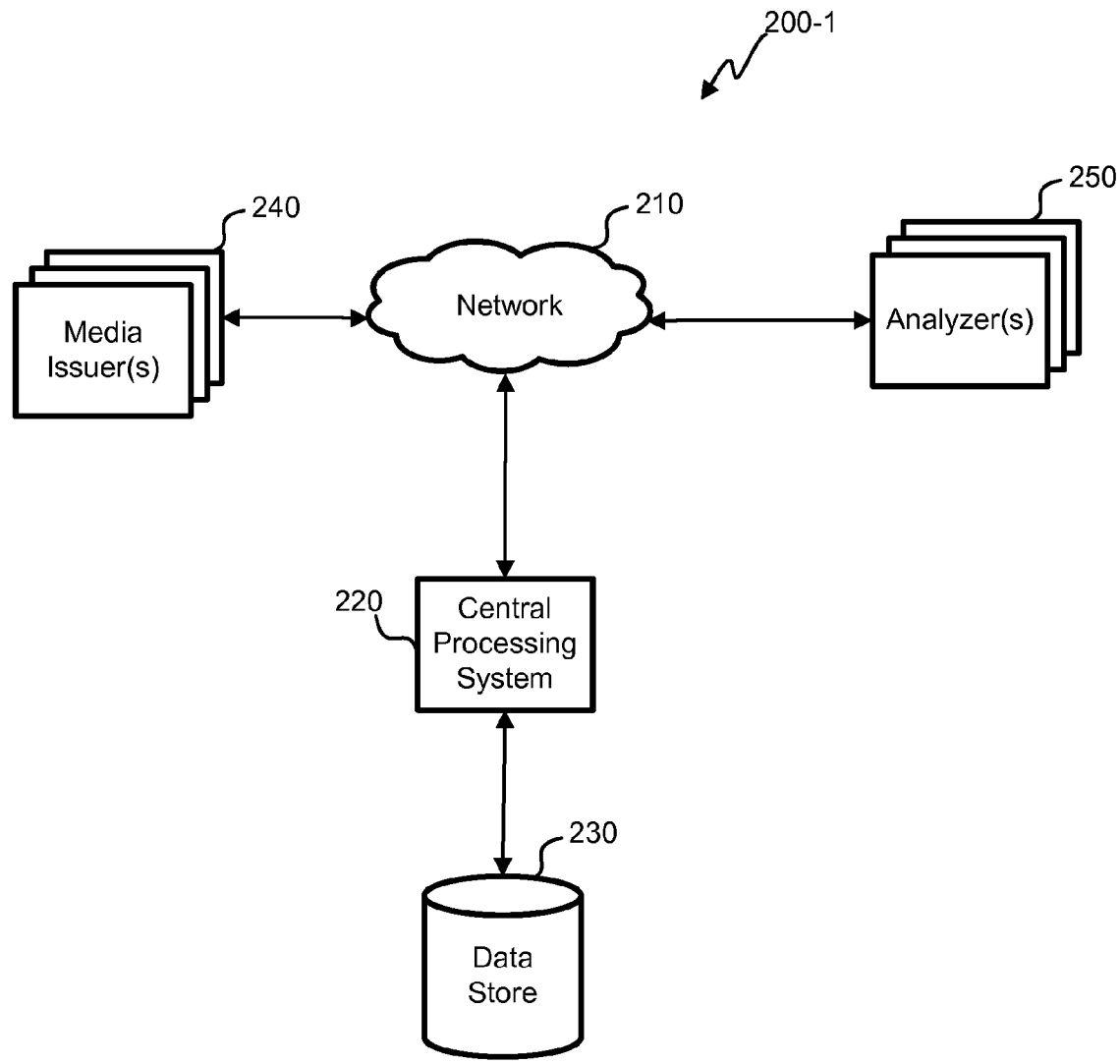
FIG. 2A is a block diagram of a first embodiment of a detection system.

Detection materials and analysis can be part of detection systems used in various types of applications. FIG. 2A illustrates a block diagram of the basic components of a detection system 200-1, according to a first embodiment. Media issuer(s) 240 can issue media to users at a first location, such as a checkpoint of a security line, a ticket booth or vending machine in a transit station, an outer entrance to a stadium, etc. An element of this embodiment is to provide some period of time from the issuance of media in which the media can be exposed to an item of interest. This exposure can occur when a user touches the media, or the media comes in contact with other items that may have come in contact with an item of interest. Such items can include clothes, luggage, purses, wallets, etc. Multiple media issuers 240 and/or analyzers 250 can be used in the detection system 200 to reduce congestion of users in the system.

The media issuer(s) 240 can include ticket feeders and/or other media-issuing devices that help ensure the media is not exposed to an item of interest beforehand. The media itself can provide a sampling particle harvesting enhanced surface, which can enhance the likelihood that items of interest remain on the surface of the media until analysis. The media issuer(s) 240 additionally can collect identification information from a user to whom the media is issued. This can include reading identification information from a government-issued identification card (e.g., drivers license) and/or gathering biometric information of the user. Collecting biometric information of the user can include taking a picture, scanning certain identifying features (e.g., fingerprint, retina, etc.), recording a voice, gathering a signature, etc. The information collected can be sent via a network 210 to a central processing system 220, which can store the information in a data store 230.

The detection system 200 also includes analyzer(s) 250 that determine whether the issued media has been exposed to an item of interest. The analyzer(s) 250 can be located at a second location to help allow time for a media to become exposed to any items of interest in the media's proximity. For example, in a transit station where media issuer(s) 240 are located in or at vending machines and/or ticket booths, the analyzer(s) can be located in or at a validator, on a platform, or in a transit vehicle. In another example, media issuer(s) 240 may be located at a checkpoint at the beginning of a security line (e.g., in an airport or a courthouse) and analyzer(s) 250 could be located at a later point in the security line (e.g., at a metal detector, after luggage x-ray, etc.). Alternatively, if a user and/or an item to which the media is attached is expected to return to a location at which media issuer(s) 240 are located, the analyzer(s) 250 can be located at the location of the media issuer(s) 240 and/or integrated with the media issuer(s) 240. Rental equipment, for example, such as luggage carts, may be returned by a user to a location at which the equipment was originally rented.

As discussed in greater detail hereafter, the analyzer(s) 250 can determine whether the media has been exposed to an item of interest by apply detection material to media and determining whether the undergoes any changes in physical and/or electrical characteristics. The analyzer(s) 150 can automatically apply the detection material to the media using application methods involving adhesive frame, sticker, magazine, or roll feed application. To help facilitate application, the detection material can be disposed on a sticker, roll of tape, clear laminate, or other material enabling the detection material to adhere to the media and react with any items of interest that may be on the media. In addition, or as an alternative, to chemical adhesion, adhesion can be created with an electrical charge, such as through negative or positive electron current flow or static electrical charge (e.g., ion charge via chemical-based reaction), and analyzer(s) 250 can be configured to create, activate, and/or expose an adhesion area on the media prior to applying the detection material.

After the detection material is applied to the media, the analyzer(s) 250 can determine whether the detection material has reacted. For example, the analyzer(s) 250 can take an image of the media to determine whether physical characteristics of a detection material (e.g., color, transparency, etc.) have changed to indicate detection of an item of interest. This analysis may also reference an image of the media that was taken before detection material was applied to the media or even before the media was issued to the user. Optionally, the media contains a background color that is encoded to be used as a quality and reference check during analysis.

In one embodiment for example, after receiving the media and before applying detection material to the media, the analyzer(s) 250 can take a first image of the media for initial reference of color and graphics. Afterwards, the analyzer(s) 250 can apply the detection material and take a second image of the media to determine a change in color with respect to the first image.

In an alternative embodiment (not shown) the media issuer(s) 240 can communicate with the analyzer(s) 250 to validate serialization, original background color for matching and card anti-cloning verification as well as transaction counting and transaction timing. Optionally, the media issuer(s) 240 and analyzer(s) 250 have check-and-balance networked communication protocol and work as a paired device(s).

The media discussed herein can include any of a variety of media types, including media provided in current transit, transportation, security, and other systems. For example, the media may comprise a fob, ticket, boarding pass, security card, or other item used for admission, access, etc. Additionally or alternatively, the media can be applied to or otherwise integrated with other items, such as a luggage cart in a hotel or airport, a tray or bin for personal items in an airport security line, a keycard for a hotel room, personal items (e.g., mobile devices, identification cards, etc), and more. The media itself can be made of one or more of a variety of materials, including but not limited to paper, plastic, glass, paper/plastic composite, and metal foil.

To help ensure the correct media is identified by the analyzer(s) 250, media can include a unique identifier. The unique identifier can include any of a variety of unique features, including numbers and/or letters. The unique identifier may be issued and/or read by the media issuer(s) 240 when issuing the media. Depending on the desired functionality of the media and/or the detection system 200, the unique identifier can be embedded on the media such that it can be read by the analyzer(s) 250 utilizing radio frequency identification (RFID), bar code scanning, optical imaging (e.g. optical pattern recognition), and/or magnetic stripe reading. Optionally, the unique identifier may contain identification information of a user, such as birth date, social security number or other government-issued identifier, name, address, phone number, email address, and/or information provided by a government-issued identification card. Moreover, the unique identifier may be encrypted, and the unique identifier also can be embedded within other information provided by the media issuer(s) 240 to the central processing system 220.

Figure 2B:
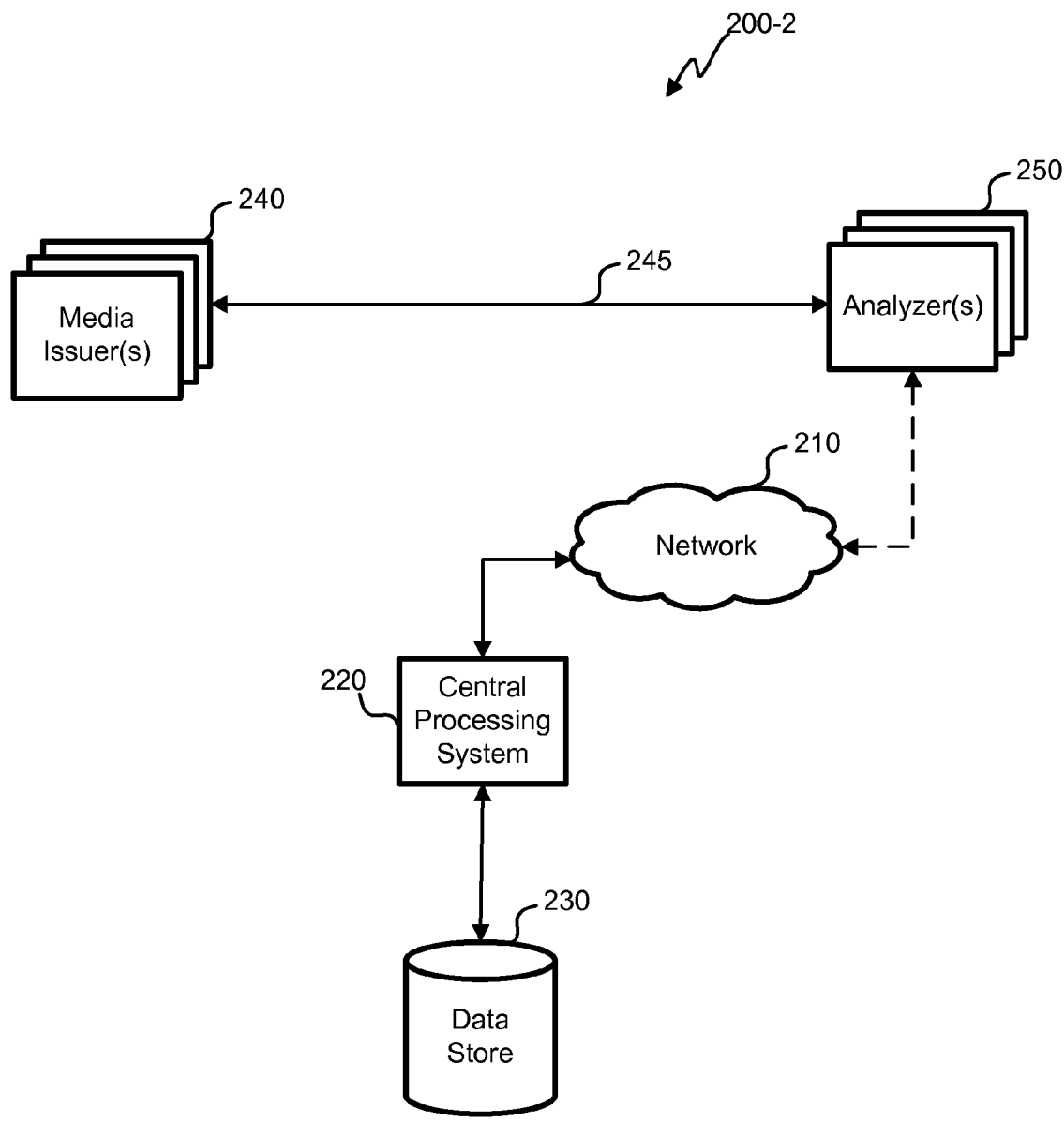
FIG. 2B is a block diagram of a second embodiment of a detection system.

FIG. 2B is a block diagram of the basic components of a detection system 200-2, according to a second embodiment. Here, media issuer(s) 240 and analyzer(s) 250 are connected directly with a communication link 245. Moreover, the media issuer(s) 240 and analyzer(s) 250 are only optionally connected via a network 210 to a central processing system 220 and data store 230. Configurations with out a network 210 and/or centralized systems 220, 230, analyzer(s) 250 and or media issuer(s), for example, can be configured to interact directly and/or provide the functionality of the central systems 220, 230.

Figure 3A:
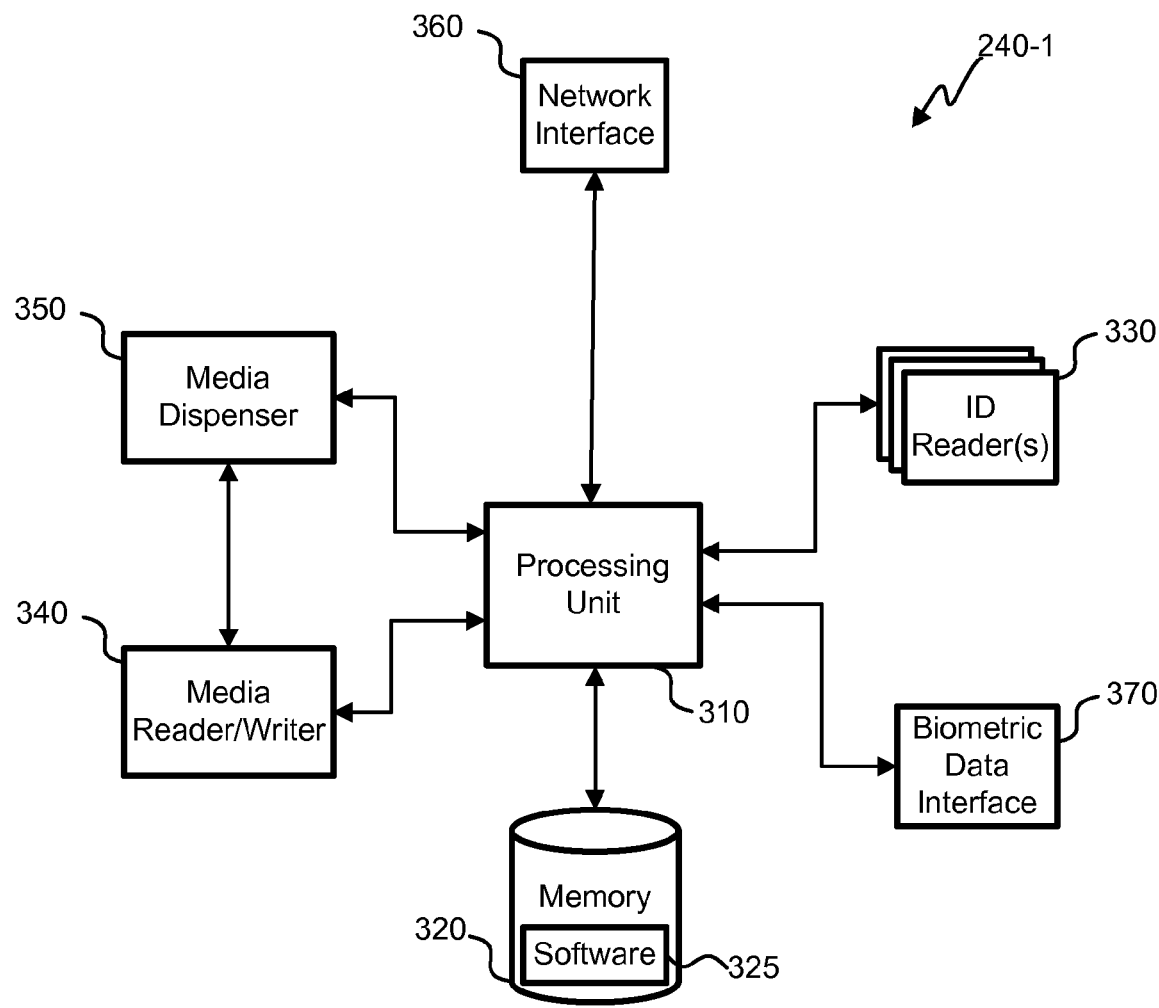
FIG. 3A is a block diagram of an embodiment of a media issuer.

FIG. 3A shows a block diagram of an embodiment of a media issuer 240-1. A processing unit 310, which can include one or more processor and/or microcontroller, runs software 325 embedded in memory 320. The memory 320 can include persistent storage such as flash, ROM, or some other non-volatile machine readable medium. The memory 320 also can be used to store unique identifiers, user information, and/or other information relating to issued media.

This embodiment of the media issuer 240-1 includes identification (ID) reader(s) 330, which can collect ID information from a user. ID reader(s) 330 can include magnetic stripe, RFID, bar code, and/or optical image readers configured to gather information from a user identifying media, such as a drivers license and/or credit card. Additionally or alternatively, the media issuer 240-1 can be connected and/or integrated with other equipment (not shown) via a biometric data interface 370 to collect biometric information from the user to which the media is issued. The equipment can include devices such as scanners and/or cameras can be to gather biometric data such as a fingerprint, signature, facial image, retinal scan, etc. This information can be utilized by the media issuer 240-1 and/or detection system 200 to determine an identity of a user, and associate the identity with a unique identifier of the media issued to the user. This association can be used later to help determine if the user has the correct media at the time of analysis of the media.

This embodiment of the media issuer 240-1 additionally includes a media dispenser 350 and a media reader/writer 340. These two components can be integrated and/or synchronized to ensure that media writer writes to the media dispensed by the media dispenser 350. The media writer 240 can write a unique identifier, which can include information specific to the media and/or to the person to whom the media is issued. Depending on the functionality of the media, the media writer 240 can write this information to the media in various ways, such as utilizing contactless/proximity technology (such as radio frequency identification RFID, ISO/IEC 14443, near-field communication (NFC), and/or other wireless techniques), electrical communication (e.g., contact smartcard technology), magnetic stripe writing, stamping, and/or printing of optical bar codes and/or other optical images or patterns.

Finally, this embodiment of the media issuer 240-1 includes a network interface 360. The network interface 360 can enable the media issuer 240-1 to communicate with other components in the detection system 200, via the network 210. The network interface 360 can utilize any of a variety of hardware and software layers to interface with the network 210. The hardware involved, for example, can utilize wireless radio frequency (RF), optical, wired, satellite, and/or other communications technologies. As shown herein, alternative embodiments can provide an interface that communicates directly with analyzer(s) 250.

Figure 3B:
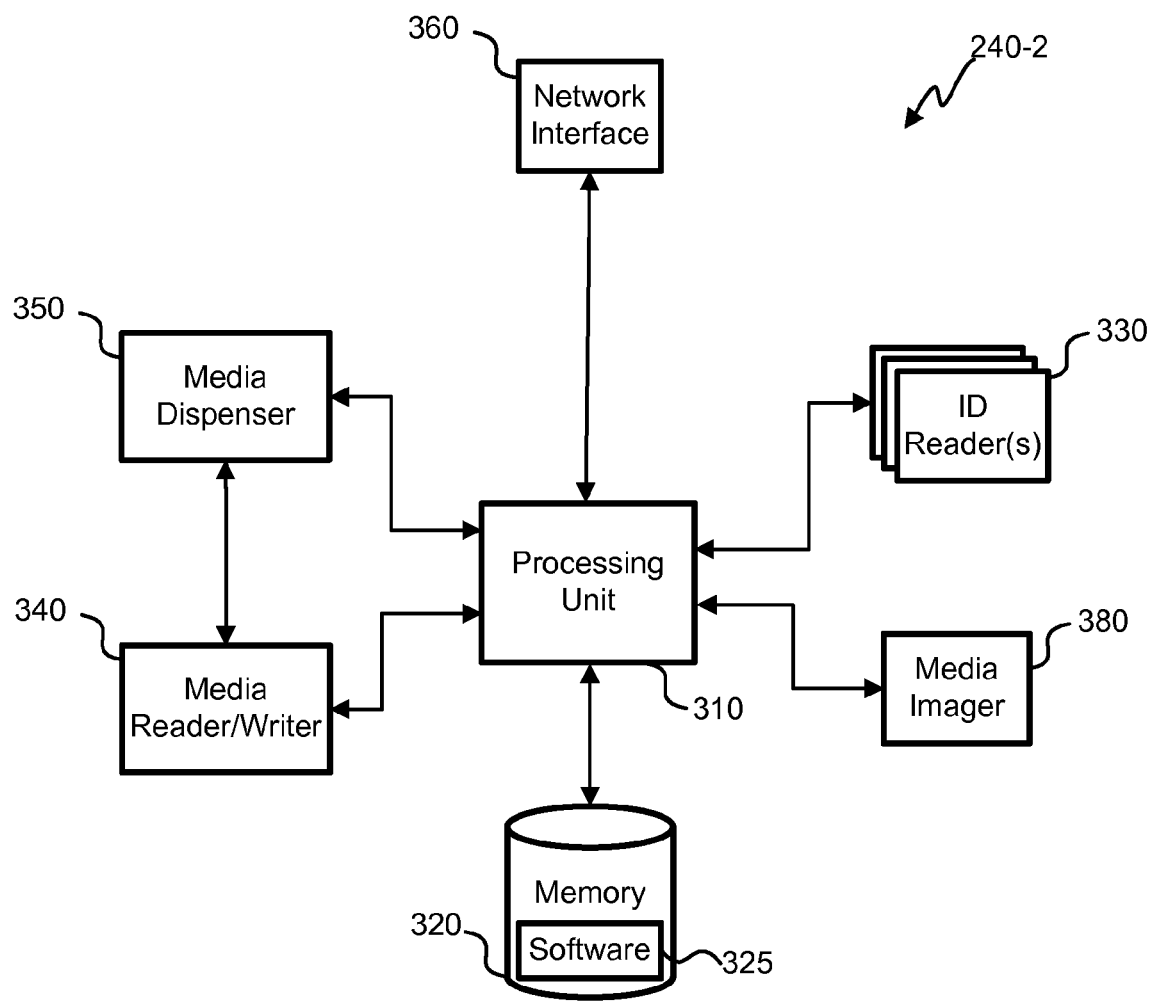
FIG. 3B is a block diagram of another embodiment of a media issuer.

FIG. 3B shows a block diagram of another embodiment of a media issuer 240-2. This embodiment illustrates how an embodiment of a media issuer 240-2 can include a media imager 380, which can comprise a camera, scanner, and/or other sensor utilizing a charge coupled device (CCD), digital light processor (DLP), infrared (IR) sensor, and/or other optical technologies. As discussed herein, some embodiments of a detection system 200 include capturing an image of media before and after application of the detection material. This can include capturing an image of the media before issuance, which can be used as a reference in later analysis of the media.

As shown in FIGS. 3A and 3B, media issuer(s) 240 can include a number of components and can be configured various ways. The embodiments of the media issuers 240-1, 240-2 illustrated are provided as examples and are not limiting. Other embodiments can include more or less components, integrate multiple components into one combined component, and/or divide functionality differently among components, depending on desired functionality. For example, where biometric data is sufficient to identify users, a media issuer 240 may not include ID reader(s) 330.

Figure 4A:
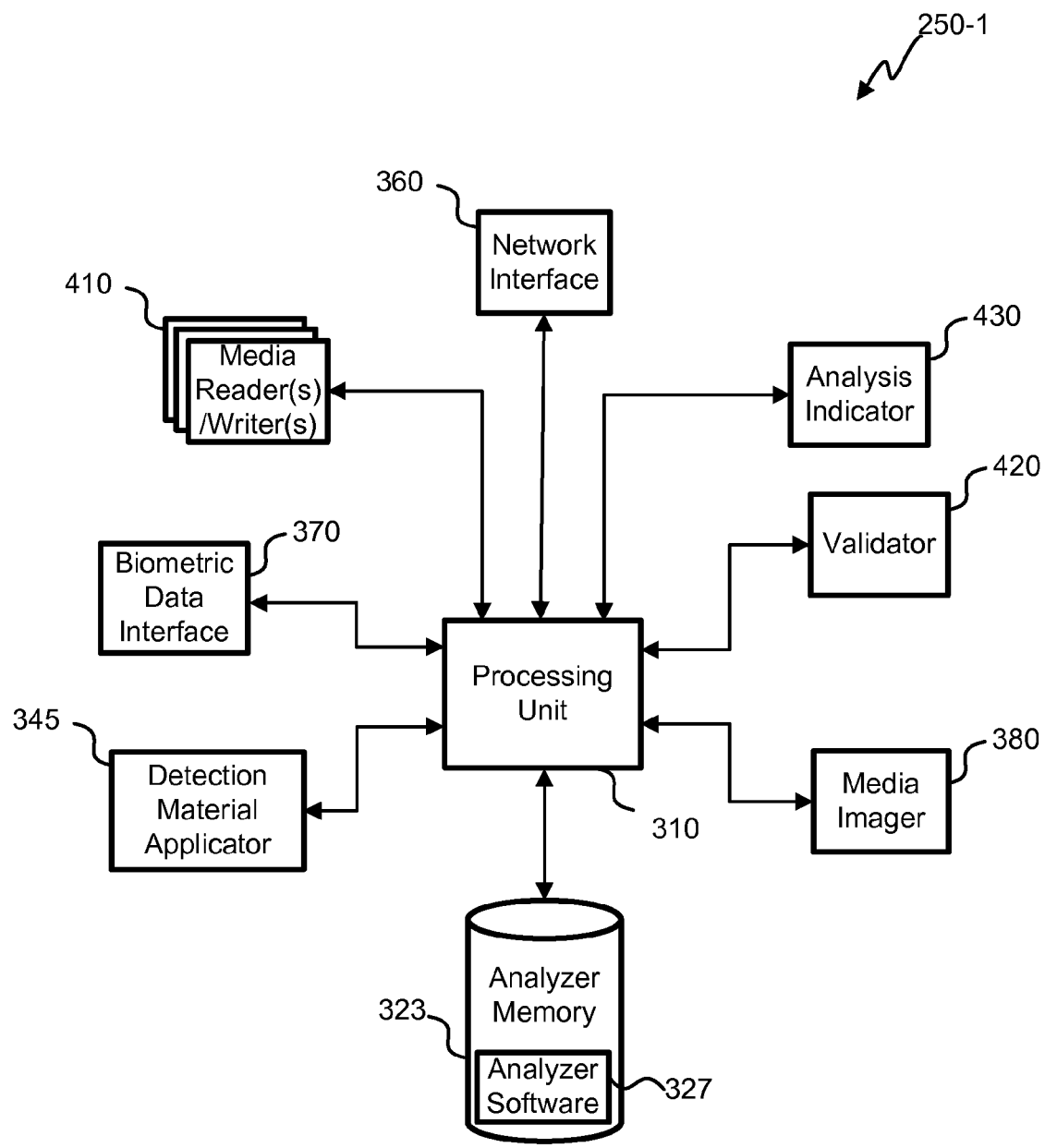
FIG. 4A is a block diagram of an analyzer, according to one embodiment.

FIG. 4A shows a block diagram of an analyzer 250-1, according to one embodiment. Similar to the media issuers 240 described herein, the analyzer 250-1 in this embodiment includes a processing unit 310, analyzer memory 323 with analyzer software 327. Also, the analyzer 250-1 includes a media imager 380 and a detection material applicator 345. According to some embodiments, the media imager 380 can be used to take two images, a first image before and a second one after the detection material is applied to the media. Because the media may have been exposed to an item of interest prior to analysis by the analyzer 250-1, the detection material can indicate exposure shortly after contact with the media. Thus, the first image can be taken prior to application of the detection material to serve as a reference. This reference image can facilitate the processing of the second image to determine whether detection material has reacted to an item of interest. For example, the images can be analyzed to determine a change or change rate in reflective light in the event a color change occurs after exposure to an item of interest. Analysis can be conducted by the processing unit 310, a remote system, and or the media imager 380. Therefore, in some embodiments, the media imager 380 can provide the additional functionality of a processing image comparator, differentiator and/or image integrator.

The determination of whether an item of interest is detected can be made by the processing unit, which can run the analyzer software 327 to process image(s) taken by the media imager 380 to determine changes in coloration, opacity, etc. Alternatively, the analyzer 250-1 can use the network interface 360 to provide information to the central processing system 220 or other processing system, via the network 210, to make the analysis. Once a result is determined, it is provided using an analysis indicator 430 and/or provided via the network interface 360 to the central processing system 220 or other remote system.

The functionality of the analysis indicator can vary, depending on cost considerations and desired functionality of the detection system 200. The indicator can be simple binary indicator such as a light-emitting diode (LED), for example, indicating detection or not. Additionally or alternatively, the indicator can indicate a more detailed result, such level(s) of detection and/or material(s) detected. This can be provided a variety of ways, including a text and/or graphical display, series of light indicators, etc. The analysis indicator 430 can be read by a human operator, who can execute appropriate security procedures based on the indicated result.

The analyzer 250-1 in the embodiment of FIG. 4A additionally can validate a media. Depending on the application of the detection system 200, a validator 420 can be integrated into the analyzer 250-1. This can provide validating functions in transit and other applications. For example, where a transit passenger is issued a ticket by a media issuer 240 at a ticket booth or vending machine, the transit passenger later can insert the ticket into the analyzer 250-1 for ticket validation.

The analyzer 250-1 can then validate the ticket an addition to analyzing the ticket to determine whether it has been exposed to an item of interest.

Additionally, the analyzer can include one or more media reader(s)/writer(s) 410 and/or a biometric data interface 370 to verify an identifier of the media and identify of the user. The media reader(s)/writer(s) 410 can determine a unique identifier of the media using technologies such as bar code or other optical scanner, RFID and/or magnetic stripe reader, etc. Once the unique identifier is determined, the analyzer can communicate with the central processing system 220 via the network interface 360 to determine an identity of a user associated with the unique identifier (the association being previously created upon issuance of the media). The analyzer 350-1 can also receive biometric data of the user from the biometric data interface 370 to verify that the user providing the media at the analyzer 350-1 is the same user to which the media was issued. Alternatively, the analyzer can provide the biometric data to the central processing system 220 and/or other remote system to verify the user. If the user is different or cannot be verified, the analyzer 250-1 can indicate accordingly to another system via the network interface 360 and/or using the analysis indicator 430. Finally, the media reader(s)/writer(s) 410 can write additional information to the media, such as an indication of the result of the detection analysis, a timestamp, and/or other information that can provide additional functionality to the media.

Figure 4B:
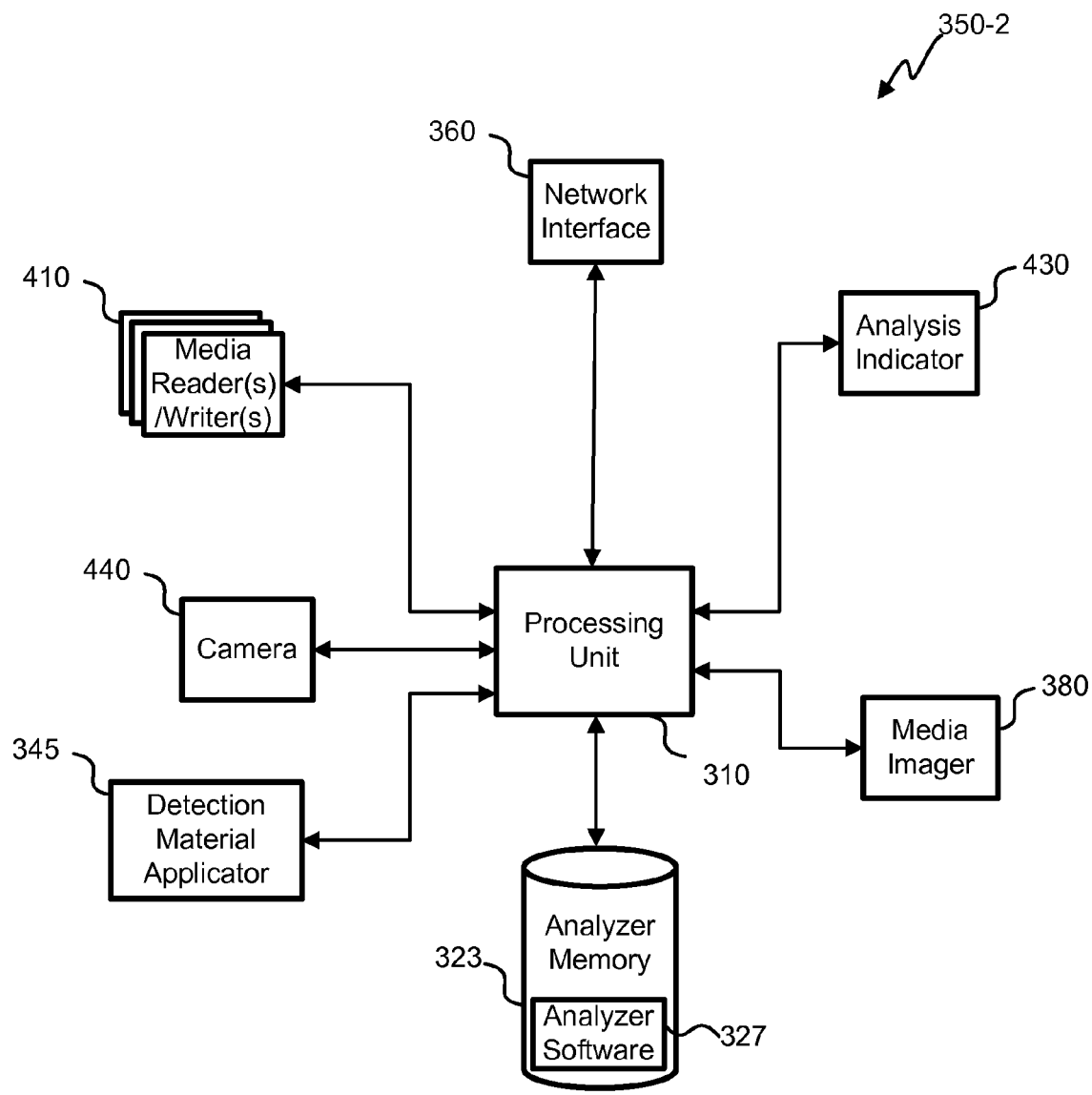
FIG. 4B is a block diagram of an analyzer, according to another embodiment.

FIG. 4B shows a block diagram of an analyzer 350-2, according to another embodiment. This embodiment includes less components and therefore provides different functionality. For example, rather than include a biometric data interface 370, this embodiment simply includes a camera 440, which can be utilized to determine and/or verify an identity of a user. In some embodiments, the camera may simply record a picture of a user associated with the media having a certain unique identifier. These latter embodiments, for example, may be included in embodiments of detection systems 300 in which an identity of a user is not determined at issuance, or verification of a user identity is not needed during analysis.

Figure 5A:
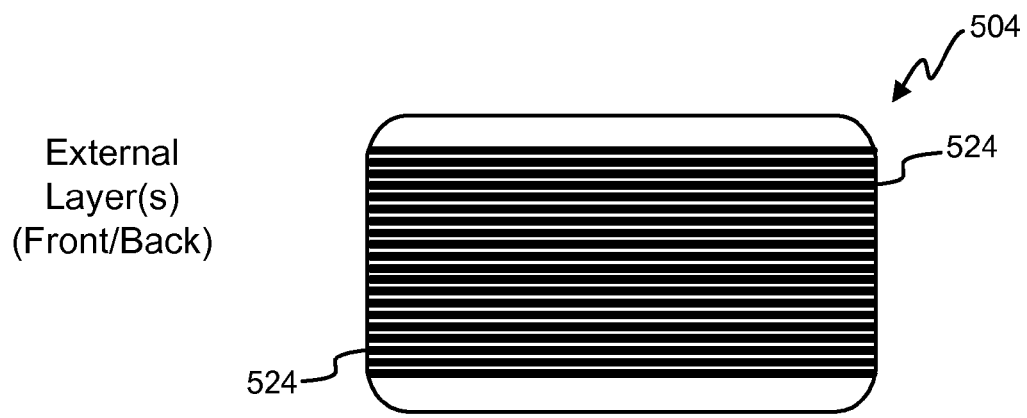
FIGS. 5A and 5B are simplified drawings of layers of a contactless smartcard that can be used as media in a detection system, according to one embodiment.
Figure 5B:
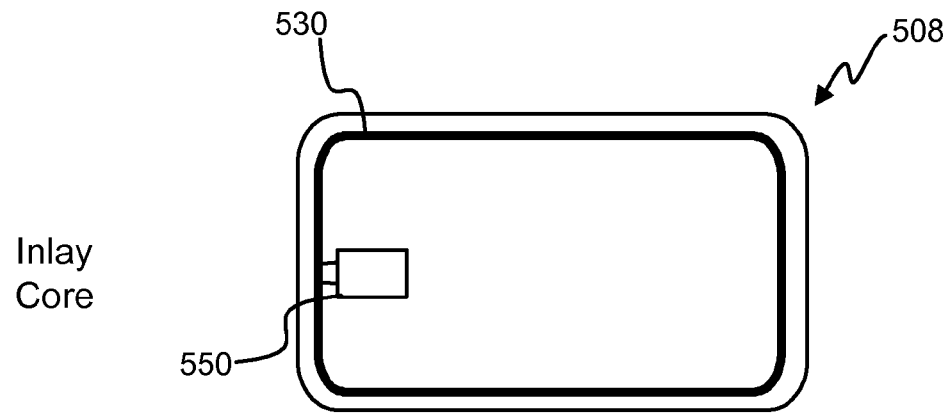

Although, as indicated herein, media of various forms can be utilized in the systems and methods described herein, FIGS. 5A and 5B illustrate a wireless smartcard that can be used as media, according to one embodiment. FIG. 5B illustrates a inlay core 508 of the smartcard, which includes an induction antenna 530 and an integrated circuit 550, which provide the wireless smartcard functionality. The overall configuration of the smart card can be changed dependent upon the requirements of the media and the ergonomics of the device, which can enhance detection from the expected handling of the smartcard.

FIG. 5A, illustrates an external layer(s) 504 of the smartcard, which can include a front and/or back layer(s). In addition to graphics and/or other features that can provide additional functionality to the smartcard, the external layer(s) 504 can include detection areas 524 to which detection material is applied to determine exposure of the media to items of interest. Detection areas 524 can include special materials and/or specially-treated surfaces that can facilitate sample harvesting of particles, including items of interest. For example, media can be manufactured in a unique manner that makes the surface of the media and/or detection areas 524 highly receptive to capturing particles as follows. The media surface structure can be manipulated to gather, capture and enhance the particle detection. In addition the media surface and/or detection areas 524 may also be smooth or glossy, dependent on the type of threat detection material. Furthermore, changes in color of detection area(s) can be compared to a color matrix to be used for a quality and reference check. The external layer(s) 504 can be made of a plastic, plasticized, polyvinyl or paper material and the locations of the detection areas 524 can vary with ergonomic requirements.

Figure 5C:
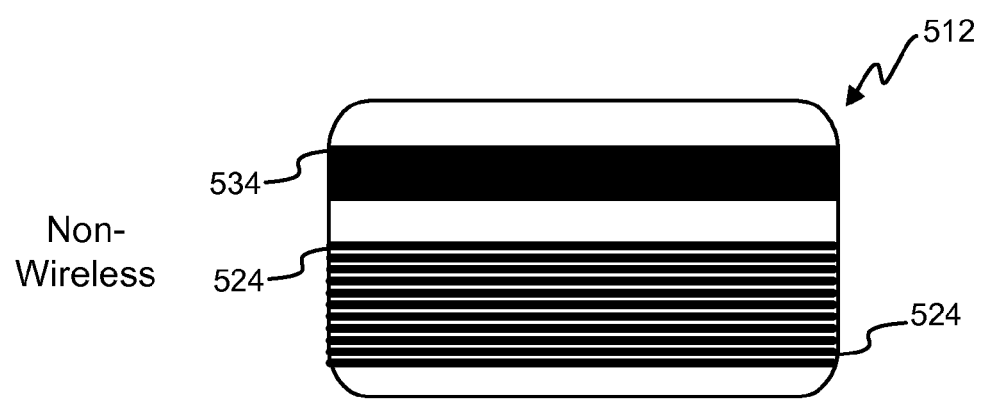
FIG. 5C is a simplified drawing of a magnetic stripe card that can be used as media in a detection system, according to one embodiment.

Other card types can be utilized in certain embodiments of the systems and methods described herein. For example, FIG. 5C illustrates a non-wireless card 512 having a magnetic stripe 534 and detection areas. Detection areas are preferably located in areas of the card where the card will be handled by a card user, which may vary by card type. Moreover, although cards conforming to the ID-1 size of the ISO/IEC 7810 standard can be used, cards of virtually any type can be integrated into detection systems and methods described herein. Embodiments of media shown in FIGS. 5A-5C are shown for illustration purposes and are not limiting, and various forms of media other than cards can be used.

Figure 6A:
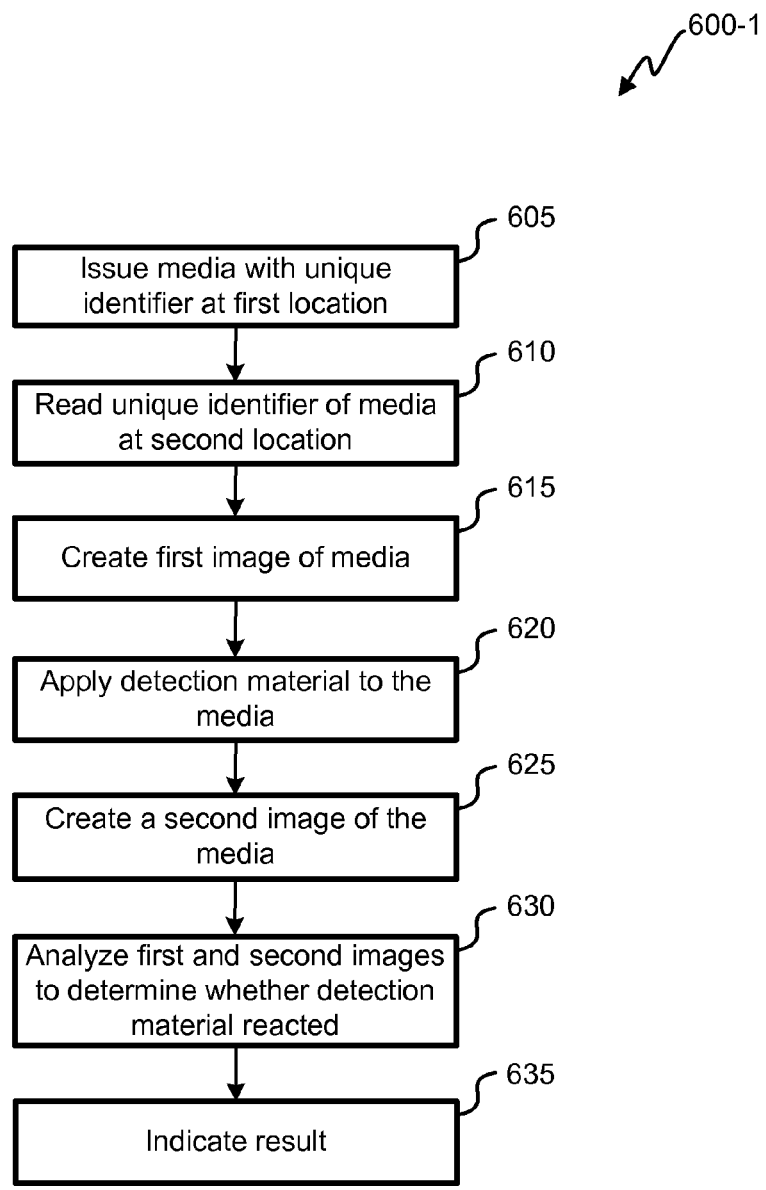
FIG. 6A is a flowchart of an embodiment of a process for determining exposure of media to an item of interest.

FIG. 6A is a flowchart of an embodiment of a process 600-1 for determining exposure of media to an item of interest. The depicted portion of the process 600-1 can begin at block 605, where the media having a unique identifier is issued at a first location. As indicated herein, the unique identifier could be written to the media at issuance and may contain information indicative of a user. The media is then subject to exposure to items of interest during a period in which the media is in the custody of a user, while traveling from the first location to a second location.

At block 610, the unique identifier of the media is read at the second location, and at block 615, a first image of the media is created. Reading the identifier of the media can identify the previously-issued media, and creating a first image of the media can provide a reference image that can be used in later analysis.

At block 620, the detection material is applied to the media. As discussed earlier, a detection material can be sensitive to certain substances, such as certain molecules or families of molecules. Thus different detection materials can be applied to different areas of the media to determine exposure to different items of interest. A predetermined amount of time may be provided after the detection material is applied and before an image of the media is taken, to provide any necessary time for detection material to react.

At block 625, a second image of the media is created, and at block 630, the first and second images are analyzed to determine whether the detection material has reacted (i.e. whether the detection material has been exposed to an item of interest). This analysis can occur at the second location, or may occur remotely, depending on desired functionality. The result of the analysis is indicated at block 635. This result can include a range of values.

Figure 6B:
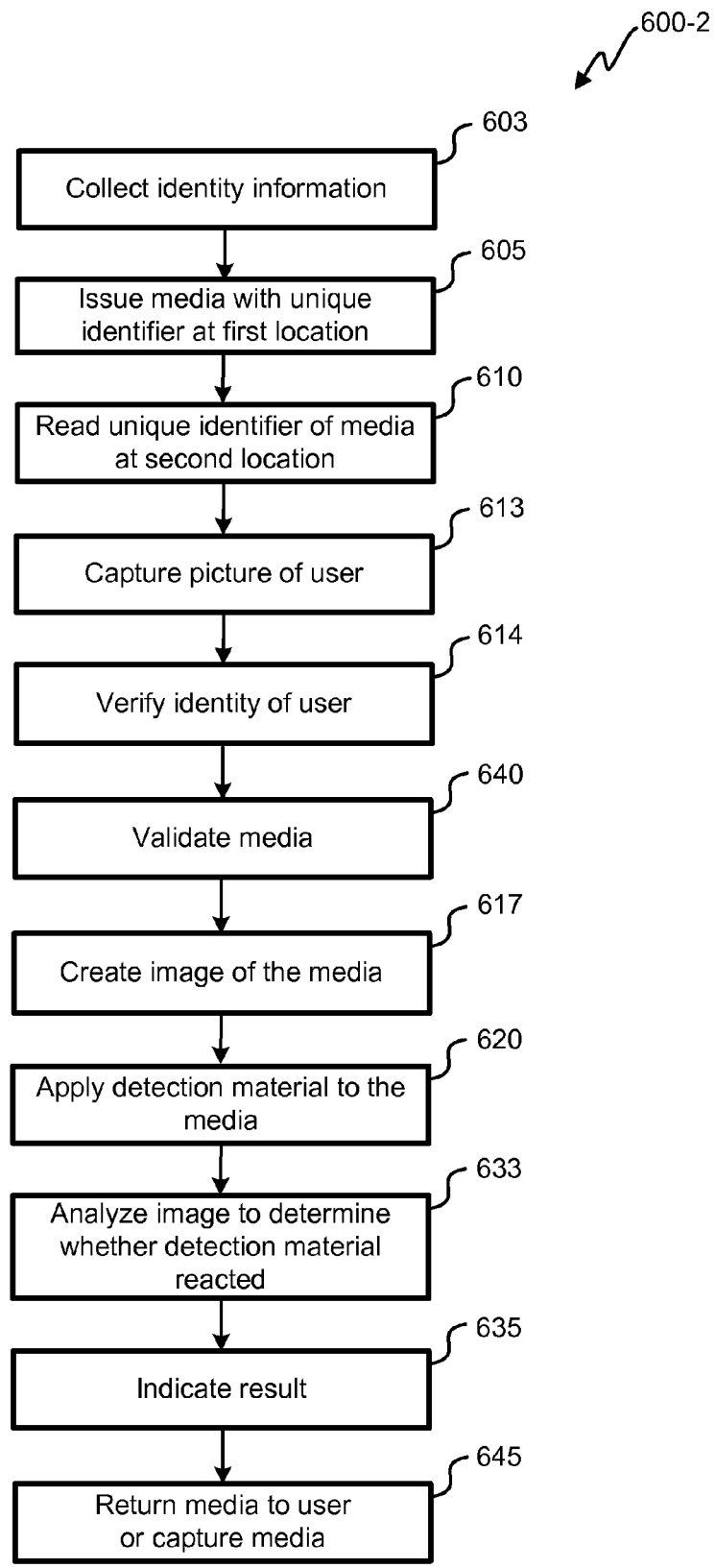
FIG. 6B is a flowchart of another embodiment of a process for determining exposure of media to an item of interest.

FIG. 6B is a flowchart of another embodiment of a process 600-2 for determining exposure of media to an item of interest, illustrating yet further contemplated features. For example, at block 603, information regarding the identity of a user can be collected. This can include biometric and/or biographic information retrieved in a database, provided by a user, read from an identification card or other identifying media, and/or captured during the issuance process. With identification information, the unique identifier can be associated with an identity of the user. This association can be made, for example, by a media issuer 240 or another component of a detection system 200.

Once the media is presented at a second location, a picture of a user is captured at block 613, and at block 617 the identify of the user is verified. Additionally or alternatively, other biometric and/or biographic information can be collected and used to verify the identity of a user. In any event, verification of a user's identity can involve retrieving information regarding the association between the user and the unique identifier of the media.

At block 617, an image of the media is created, and at block 633 the image is analyzed to determine whether the detection material has reacted. Unlike the process 600-1 of FIGS. 6A, this process 600-2 analyzes a single image. Such single-image analyses are contemplated where the detection material and media imaging are sufficiently accurate to provide a reliable analysis.

At block 640, the media is validated. As described herein, embodiments can incorporate other features, such as ticket validation, to provide additional functionality to the user. In so doing, not only is overall security increased, but individual users are provided an additional convenience.

Finally, at block 645, the media is returned to the user or captured. As discussed hereinabove, whether the media is returned to the user or captured can depend on whether an item of interest was detected, a type of item of interest detected, and/or a value or level of detection. Moreover, other factors (e.g. information regarding the user, a security threat level, a time of day, etc.) can be considered in the determination of whether to return the media. Captured media can be preserved for further analysis and/or processing.

Figure 6C:
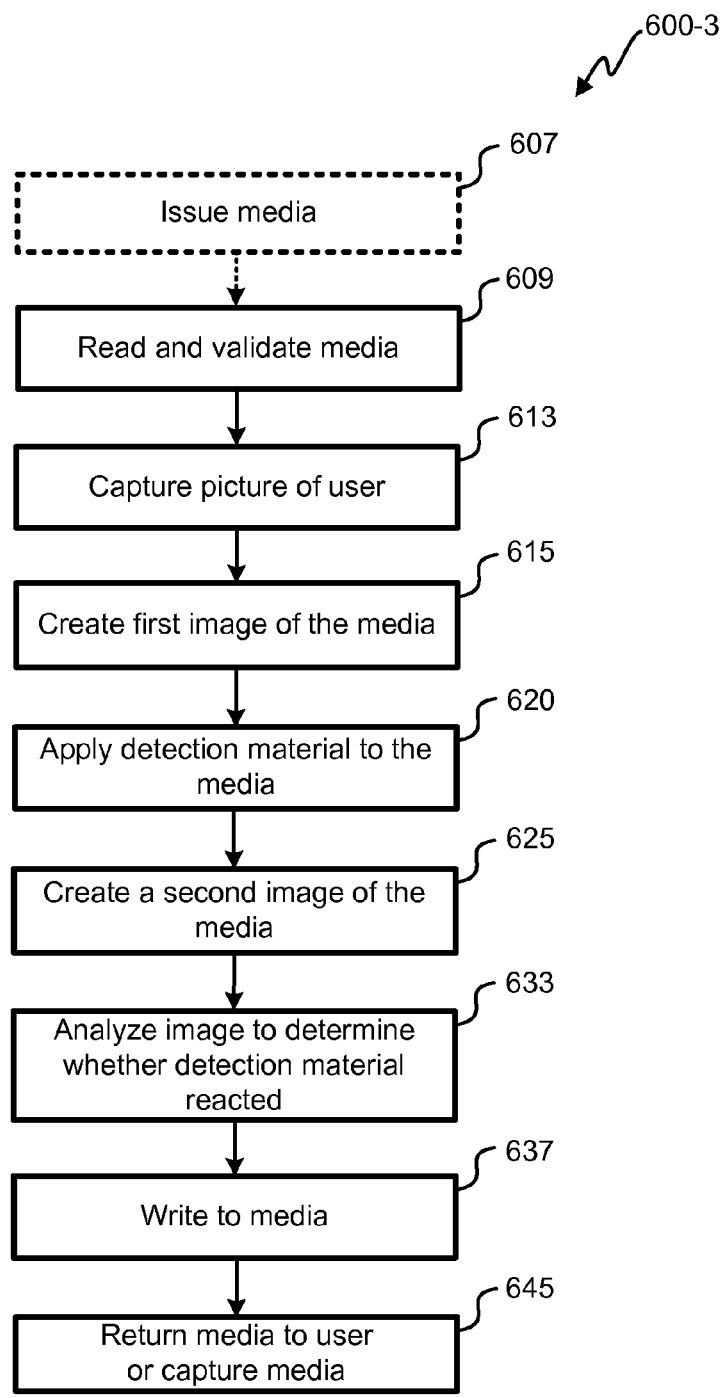
FIG. 6C is a flowchart of yet another embodiment of a process for determining exposure of media to an item of interest.

FIG. 6C is a flowchart of yet another embodiment of a process 600-3 for determining exposure of media to an item of interest, illustrating how processes contemplated herein can be further altered and adapted. The process 600-3, for example, can be carried out by validator units 145 such as those discussed in the detection system 100-1 utilized in a public transit system, as shown in FIG. 1A. The process begins at block 607, where the media is issued. However, this step may not be needed (as indicated by the dotted line) in certain cases, such as where media is provided by a third party, or is reusable (e.g. identification or security cards).

At block 609 the media is read and validated before undergoing a process (blocks 613-633) similar to those shown in FIGS. 6A and 6B. Here, however, no unique identifier is read from the card. Nonetheless, the picture of the user, taken at block 613, can be used to associate the user with a particular media.

Another feature shown in this process 600-3 is, at block 637, data can be written to the media. The information can include detection/non-detection information, such as a timestamp, location, what item(s) of interest was detected, and/or levels of detection. Other information (e.g., transit data) can also be written to provide additional functionality to the media. Depending on the type of media, data can be written using contactless/ proximity or other radio frequency (RF) technology, electrical signals, magnetic stripe writing, stamping, and/or printing of optical bar codes and/or other optical images or patterns.

A number of variations and modifications of the disclosed embodiments can also be used. For example, the processes depicted in FIGS. 6A-6C are not limiting and can include more or less blocks, may combine or separate features of a particular blocks, or rearrange order of blocks while keeping within the spirit of this disclosure. Embodiments could be embedded into any human-transported item. Furthermore, embodiments described herein regarding contactless smartcards can apply similarly to smartcards with contacts. Also, as indicated earlier, media can be issued and analyzed at the same location. Depending on the result of a detection analysis, an analyzer 250 can route the media to a capture bin or issue to an external feeder for human exchange.

Figure 7A:
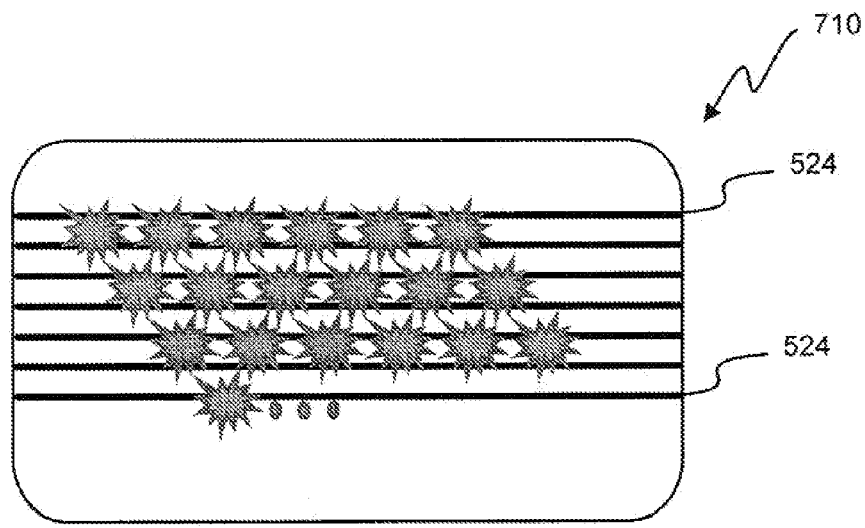
FIG. 7A is a simplified drawing of media having a non-symmetric surface hole structure, according to one embodiment.
Figure 7B:
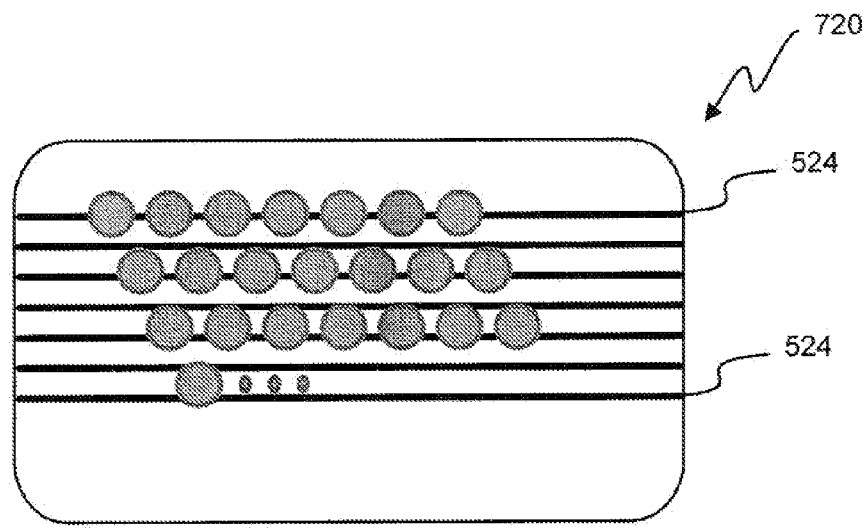
FIG. 7B is a simplified drawing of media having a symmetric surface hole structure, according to another embodiment.

FIGS. 7A and 7B illustrate additional embodiments of media that can be utilized in the systems and methods described herein. For example, FIG. 7A shows a media 710 having non-symmetric, geometrically-spaced holes in one or more layers of the media 710 that are used to capture particles, including items of interest. The holes can also enhance particle detection, and they may be rough or non-symmetrical, and/or smooth or symmetrical, as shown by media 720 in FIG. 7B. The holes can be under or over the polymer detection area(s) 524.

The disclosure has focused on detecting items of interest by using images of media to determine changes in physical characteristics of a detection material. Other methods can be used, however, additionally or alternatively, to determine whether the detection material has been exposed to an item of interest. For example, where a detection system 100 utilizes detection materials that have electrical properties that change upon exposure to an item of interest, one or more electrical readings (e.g., conductivity, capacitance, inductance, etc.) can be taken by an analyzer 250 before and/or after application of the detection material to the media. Electrical measurement reader(s) can thereby be used in addition or as an alternative to a media imager(s) 380.

Additionally, components shown in various diagrams detailed herein can include additional functionality. For example, components described as "readers" or "writers" can include proximity coupling devices (PCDs) that include both reading and writing capabilities. Other components can be similarly combined to form multi-functional units. Conversely, components having multiple functions may be separated into functionally distinct units.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

The term "machine-readable medium" includes, but is not limited to portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

While the principles of the disclosure have been described above in connection with specific apparatuses and methods, it is to be clearly understood that this description is made only by way of example and not as limitation on the scope of the disclosure.

What is claimed is:

1. A method of determining exposure of a media to an item of interest, the method comprising:
   providing the media at a first location, wherein the media has a unique identifier;
   determining the unique identifier of the media at a second location;
   creating, at the first location, a first image of the media;
   applying, to the media, detection material sensitive to the item of interest, wherein:
   the item of interest is one of a chemical, a biologic compound, or an explosive; and
   the applying occurs at the second location;
   creating, at the second location, a second image of the media;
   analyzing the first image and the second image to determine if the detection material has sensed the item of interest, wherein the analyzing includes determining an optical change between the first image and the second image; and
   indicating a result based, at least in part, on the analyzing.

2. The method of determining exposure of the media to the item of interest as recited in claim 1, wherein the first image of the media, the second image of the media, or both, utilize at least one optical technology from the group consisting of:
   a charge coupled device (CCD),
   a digital light processor (DLP), and
   an infrared (IR) sensor.

3. The method of determining exposure of the media to the item of interest as recited in claim 1, wherein the creating the first image of the media occurs at the second location.

4. The method of determining exposure of the media to the item of interest as recited in claim 1, further comprising determining an identity of a user.

5. The method of determining exposure of the media to the item of interest as recited in claim 4, further comprising associating the identity of the user with the unique identifier of the media.

6. The method of determining exposure of the media to the item of interest as recited in claim 5, further comprising verifying, at the second location, the identity of the user.

7. The method of determining exposure of the media to the item of interest as recited in claim 4, wherein the determining the identity of the user includes capturing a picture of the user.

8. The method of determining exposure of the media to the item of interest as recited in claim 1, wherein the determining the unique identifier of the media at the second location includes using at least one technology from the group consisting of:
   radio frequency identification (RFID),
   bar code scanning,
   optical imaging, and
   magnetic stripe reading.

9. The method of determining exposure of the media to the item of interest as recited in claim 1, wherein applying detection material to the media includes using an adhesive frame, sticker, magazine, or roll feed.

10. The method of determining exposure of the media to the item of interest as recited in claim 1, further including creating, at the second location, an adhesive area on the media.

11. The method of determining exposure of the media to the item of interest as recited in claim 10, wherein the creating the adhesive area on the media includes at least one of:
   applying an adhesive material to the media, or
   exposing an adhesive material of the media.

12. The method of determining exposure of the media to the item of interest as recited in claim 10, wherein the adhesive area causes adhesion of particles using at least one of:
   chemical adhesion, or
   electrical charge.

13. A device for determining exposure of a media to an item of interest, the device comprising:
   a media imager configured to create at least one image of the media at a first location;
   a detection material applicator configured to apply, to the media, detection material sensitive to the item of interest, wherein the item of interest is one of a chemical, a biologic compound, or an explosive;
   a processing unit configured to analyze, at a second location, the at least one image of the media to determine if the detection material has sensed the item of interest based, at least in part, on an optical characteristic of the detection material in the at least one image; and
   an analysis indicator configured to indicate a result based, at least in part, on an analysis of the at least one image of the media.

14. The device for determining exposure of the media to the item of interest as recited in claim 13, wherein the media imager is configured to create a first image and a second image, the first image being created before the detection material is applied to the media, and the second image being created after the detection material is applied to the media.

15. The device for determining exposure of the media to the item of interest as recited in claim 14, wherein the processing unit is configured to determine if the detection material has sensed the item of interest based, at least in part, on an optical change of the detection material between the first image and the second image.

16. The device for determining exposure of the media to the item of interest as recited in claim 13, further comprising a camera configured to capture a picture of a user of the media.

17. The device for determining exposure of the media to the item of interest as recited in claim 13, further comprising a media reader configured to determine a unique identifier of the media.

18. The device for determining exposure of the media to the item of interest as recited in claim 17, further comprising an identification verifier configured to verify an identity of a user of the media.

19. The device for determining exposure of the media to the item of interest as recited in claim 18, wherein the processing unit is further configured to verify the identity of the user of the media based, at least in part, on a picture of the user and the unique identifier of the media.

20. The device for determining exposure of the media to the item of interest as recited in claim 13, wherein the media reader includes at least one device from the group consisting of:
   a radio frequency identification (RFID) reader,
   a bar code scanner,
   an optical imager, and
   a magnetic stripe reader.

21. The device for determining exposure of the media to the item of interest as recited in claim 13, wherein the detection material applicator is configured to use an adhesive frame, sticker, magazine, or roll feed application.

22. The device for determining exposure of the media to the item of interest as recited in claim 13, wherein the analysis indicator includes at least one item from the group consisting of:

a display,
a light-emitting diode (LED),
a speaker, and
a network interface.

23. A non-transitory machine-readable storage medium comprising instructions embodied thereon that, when executed by at least one machine, cause the at least one machine to:
    determine a unique identifier of the media;
    create a first image of the media, at a first location;
    apply, to the media, detection material sensitive to the item of interest, wherein the item of interest is one of a chemical, a biologic compound, or an explosive;
    create a second image of the media, at a second location;
    analyze the first image and the second image to determine if the detection material has sensed the item of interest, wherein the analyzing includes determining an optical change between the first image and the second image; and
    indicate a result based, at least in part, on the analyzing.

24. The non-transitory machine-readable storage medium as recited in claim 23, wherein the instructions, when executed by at least one machine, further cause the at least one machine to:
    provide the media at the first location.

25. The non-transitory machine-readable storage medium as recited in claim 23, wherein the instructions, when executed by at least one machine, further cause the at least one machine to determine an identity of a user.

26. The non-transitory machine-readable storage medium as recited in claim 25, wherein the instructions, when executed by at least one machine, further cause the at least one machine to associate the identity of the user with the unique identifier of the media.

27. The non-transitory machine-readable storage medium as recited in claim 26, wherein:
    associating the identity of the user with the unique identifier of the media is configured to occur at the first location; and
    the instructions, when executed by at least one machine, further cause the at least one machine to verify, at the second location, the identity of the user.

28. The non-transitory machine-readable storage medium as recited in claim 25, wherein determining the identity of the user includes capturing a picture of the user.

29. The non-transitory machine-readable storage medium as recited in claim 23, wherein the determining the unique identifier of the media includes using at least one technology from the group consisting of:
    radio frequency identification (RFID),
    bar code scanning,
    optical imaging, and
    magnetic stripe reading.

30. The non-transitory machine-readable storage medium as recited in claim 23, wherein the instructions, when executed by at least one machine, further cause the at least one machine to apply the detection material to the media includes using an adhesive frame, sticker, magazine, or roll feed application.

31. The non-transitory machine-readable storage medium as recited in claim 23, wherein the instructions, when executed by at least one machine, further cause the at least one machine to create an adhesive area on the media.

32. The non-transitory machine-readable storage medium as recited in claim 31, wherein the creating the adhesive area on the media includes at least one of:
    applying an adhesive material to the media, or
    exposing an adhesive material of the media.

33. The non-transitory machine-readable storage medium as recited in claim 31, wherein the adhesive area is created to adhere particles using at least one of:
    chemical adhesion, or
    electrical charge.

* * * * *